(12) United States Patent
Qin et al.

(10) Patent No.: US 11,690,738 B2
(45) Date of Patent: Jul. 4, 2023

(54) STENT AND PREPARATION METHOD THEREFOR

(71) Applicant: Biotyx Medical (Shenzhen) Co., Ltd., Shenzhen (CN)

(72) Inventors: Li Qin, Shenzhen (CN); Wenjiao Lin, Shenzhen (CN)

(73) Assignee: Biotyx Medical (Shenzhen) Co., Ltd., Shenzhen (CN)

( * ) Notice: Subject to any disclaimer, the term of this patent is extended or adjusted under 35 U.S.C. 154(b) by 244 days.

(21) Appl. No.: 16/768,286

(22) PCT Filed: Oct. 17, 2018

(86) PCT No.: PCT/CN2018/110568
§ 371 (c)(1),
(2) Date: May 29, 2020

(87) PCT Pub. No.: WO2019/109736
PCT Pub. Date: Jun. 13, 2019

(65) Prior Publication Data
US 2020/0289297 A1   Sep. 17, 2020

(30) Foreign Application Priority Data

Dec. 6, 2017 (CN) .......................... 201711277320.1

(51) Int. Cl.
*A61F 2/82* (2013.01)
*A61F 2/915* (2013.01)

(52) U.S. Cl.
CPC ...... *A61F 2/82* (2013.01); *A61F 2002/91583* (2013.01); *A61F 2240/001* (2013.01); *A61F 2250/0098* (2013.01)

(58) Field of Classification Search
CPC .............. A61F 2/82; A61F 2002/91583; A61F 2240/001; A61F 2250/0098; A61F 2002/91575; A61F 2/915
See application file for complete search history.

(56) References Cited

U.S. PATENT DOCUMENTS 6,758,859 B1 *  7/2004  Dang ...................... A61F 2/915
                                                          623/1.42
2007/0156230 A1   7/2007  Dugan et al.
(Continued)

FOREIGN PATENT DOCUMENTS

| CN | 106333773 A | 1/2017 |
| CN | 107405432 A | 11/2017 |
| WO | 2017005107 A1 | 1/2017 |

OTHER PUBLICATIONS

Indian Office Action dated Jun. 27, 2021, in connection with corresponding IN Application No. 202027028379; 6 pages.
(Continued)

*Primary Examiner* — Keri J Nelson
*Assistant Examiner* — Rebecca Lynee Zimmerman
(74) *Attorney, Agent, or Firm* — Maier & Maier, PLLC

(57) ABSTRACT

A stent and a preparation method therefor. The stent includes a stent substrate. The stent substrate is provided with at least one radiopaque structure thereon. Each radiopaque structure includes at least one radiopaque unit. A radiopaque material is inlaid in each radiopaque unit, and a ratio of the volume of the radiopaque material to the volume of the radiopaque unit ranges from 1.1 to 1.4. By the stent and the preparation method therefor, the interference fit between the radiopaque material and the radiopaque unit can be better implemented, so that the radiopaque material and the radiopaque unit have strong bonding force therebetween, and the problem of embolism caused by the drop of a radiopaque material is avoided.

9 Claims, 1 Drawing Sheet

(56) References Cited

U.S. PATENT DOCUMENTS

2008/0215129 A1      9/2008  Venturelli et al.
2016/0361182 A1*   12/2016  Lumauig .................. B21J 15/14
2017/0071764 A1      3/2017  Dugan et al.

OTHER PUBLICATIONS

Extended European Search Report dated Jul. 19, 2021, in connection with corresponding EP Application No. 18885272.7; 8 pages.
International Search Report dated Dec. 29, 2018 in corresponding International Application No. PCT/CN2018/110568; 6 pages.

* cited by examiner

STENT AND PREPARATION METHOD THEREFOR

FIELD

Embodiments relate to the field of interventional medical devices, and more particularly, to a stent and a preparation method thereof.

BACKGROUND

Digital subtraction angiography (DSA) is the most commonly used auxiliary positioning device for an interventional medical instrument, such as stent implantation. Its principle is as follows: when the radiation density of a stent material is greater than the density of tissues or organs around an implantation site, a contrast image is formed under X-rays for doctors to diagnose or perform clinical treatment. At present, the materials used to prepare the stent are mainly metals and polymers. When a stent is made of a metal material with relatively high radiation density, such as cobalt chromium alloy, medical stainless steel, etc., and the wall thickness of the stent is more than 70 microns, an image of the stent itself under the DSA device is obvious, and can be used by doctors for diagnosis or clinical treatment. When a stent is made from a material with relatively low radiation density, such as polylactic acid, magnesium alloy, etc., although the wall thickness of the stent is up to 120 microns or more, the stent is almost invisible under the DSA device. Alternatively, when a stent is made from a metal material with relatively high radiation density, and the thickness of the stent is less than 70 microns, an image of the stent itself is not obvious under the DSA device. In both the above two cases, the position and profile of the stent cannot be recognized by naked eyes, so it is necessary to improve the visibility of the stent.

At present, the wall thicknesses of commercially available metal vascular stents with relatively high radiation density are all above 70 microns. However, with the developments of clinical research, it has been found that the smaller the thickness of a vascular stent, the better the wall adherence of the stent, and the smaller the shear interference to the blood flow of the stent segment, and thus the lower the risk of thrombosis. Therefore, it is foreseeable that a thin wall thickness stent is one of the development trends of vascular stents in the future. However, such thin wall thickness stent would have poor visibility under DSA.

Therefore, for polymer stents and thin wall thickness metal stents with poor visibility under DSA, it is necessary to design a radiopaque structure in an appropriate position of the stent and fill a radiopaque material into the radiopaque structure, such that the stent can be identified under DSA to assist doctors to accurately judge the position and profile of the stent. The design principle of the radiopaque structure is to design a smaller size, so as to not affect the mechanical properties of the stent. The currently used radiopaque material filled with the radiopaque structure is a noble metal with high radiation density, such as gold, platinum, etc., to ensure that the radiopacity can be achieved with the smallest radiopaque structure size.

At present, the radiopaque material is inlaid in the radiopaque structure by mechanical pressure riveting. However, the approach has many disadvantages. First, during the pressure riveting process, due to the small size of the radiopaque structure, the work efficiency is relatively low when operating under a microscope. Meanwhile, a rivet needle used for pressure riveting is easy to damage the stent and change the surface of the stent. After the stent is implanted into the body, it may result in thrombus risk. Second, the radiopaque material and the radiopaque structure can achieve an interference fit along a normal direction of a contact surface to fully fix the radiopaque material. However, during pressure riveting, if a relatively soft radiopaque material, such as gold, is used, it sometimes flows out of the radiopaque structure. If part of the radiopaque material flows out of the radiopaque structure, it will not be able to achieve an interference fit with the radiopaque structure, such that the radiopaque material is insufficient in fixing force and tends to drop during the implantation procedure, which may cause embolism. If a relatively hard radiopaque material, such as platinum, is used, it may crack or break the radiopaque structure, resulting in a great risk of falling of the radiopaque material during the stent implantation procedure, which may cause embolism. Finally, during the mechanical pressure riveting process, it is also possible that the radiopaque material does not flow out of the radiopaque structure, but the radiopaque material is deformed during the pressure riveting process. That is, the shape of the radiopaque material is inconsistent with the shape of the radiopaque structure, resulting in a gap with a part in contact with the radiopaque structure and an insufficient fixing force of the radiopaque material. Therefore, the radiopaque material tends to drop during and after implantation of the stent, which may cause embolism. The smaller the wall thickness of the stent, the higher the risk of occurrence of these defects. The above problems that may be introduced by current mechanical pressure riveting of the radiopaque materials need to be solved.

SUMMARY

In view of this, it is necessary to address the problem of insufficient fixing force between the radiopaque material and the radiopaque structure when the radiopaque material is inlaid in the radiopaque structure by the existing mechanical pressure riveting method, and to provide a solution to prevent the radiopaque material from dropping due to mechanical pressure riveting.

Thus, embodiments include a stent, including a stent substrate, which is provided with at least one radiopaque structure thereon, where each of the radiopaque structures includes at least one radiopaque unit, and a radiopaque material is inlaid in each of the radiopaque units; and a ratio of the volume of the radiopaque material to the volume of the radiopaque unit is 1.1 to 1.4.

In one embodiment, a ratio of the volume of the radiopaque body to the volume of the radiopaque unit is 1.2 to 1.4.

In one embodiment, there are two radiopaque structures which are respectively disposed at two ends of the stent substrate; and each of the radiopaque structures includes four radiopaque units, the four radiopaque units being arranged in a petal shape.

In one embodiment, the radiopaque body includes a radiopaque material; and the radiopaque material is selected from at least one of gold, platinum, osmium, rhenium, tungsten, iridium, rhodium, tantalum, barium sulfate, niobium trioxide, titanium oxide, zirconia, elemental iodine, and iodide.

In one embodiment, the radiopaque body further includes a binder, and the binder is a degradable polymer.

In one embodiment, the wall thickness of the stent substrate is less than or equal to 150 microns.

In one embodiment, the wall thickness of the stent substrate is less than or equal to 70 microns.

In one embodiment, a projection area of the radiopaque material in an X-ray incident direction is less than or equal to 0.5 mm$^2$.

Further, a preparation method for a stent is provided.

A preparation method for a stent includes the following steps:

providing a stent substrate on which at least one radiopaque structure is disposed, where each of the radiopaque structures includes at least one radiopaque unit;

providing a radiopaque material, and pre-shaping the radiopaque material according to a shape of the radiopaque unit to form a blocky radiopaque material;

perform a cold treatment on the blocky radiopaque material, such that the blocky radiopaque material shrinks; and placing the radiopaque material subjected cold shrinkage in the radiopaque unit, and then heating to expand the blocky radiopaque material subjected to cold shrinkage to inlay in the radiopaque unit.

In one embodiment, the temperature of the cold treatment is −20° C. to −80° C.

In one embodiment, the time of the cold treatment is more than or equal to 30 min.

In one embodiment, the step of heating may be interpreted as that the blocky radiopaque material subjected to cold shrinkage is placed in the radiopaque unit, and then naturally warms up to room temperature.

In one embodiment, the step of providing the radiopaque material, and preshaping the radiopaque material according to the shape of the radiopaque unit to form the blocky radiopaque material may be interpreted that the radiopaque material is pre-shaped in a mold to form the blocky radiopaque material that matches the radiopaque unit in shape.

In one embodiment, in the step of providing the radiopaque material, and preshaping the radiopaque material according to the shape of the radiopaque unit to form the blocky radiopaque material, the size of the blocky radiopaque material in a normal direction of a contact surface is larger than the size of the radiopaque unit in the normal direction of the contact surface.

The radiopaque material of the stent is inlaid in the radiopaque unit, and the ratio of the volume of the radiopaque material to the volume of the radiopaque unit is 1.1 to 1.4. In this way, the interference fit between the radiopaque material and the radiopaque unit can be better achieved, so that the radiopaque material and the radiopaque unit have a strong bonding force therebetween, and the problem of embolism caused by the drop of the radiopaque material is avoided.

DETAILED DESCRIPTION OF THE EMBODIMENTS

In order to have a clearer understanding of the technical features, objects and effects of the present disclosure, embodiments will now be described in detail with reference to the drawings, but the scope of protection is not limited thereto.

Figure 1:
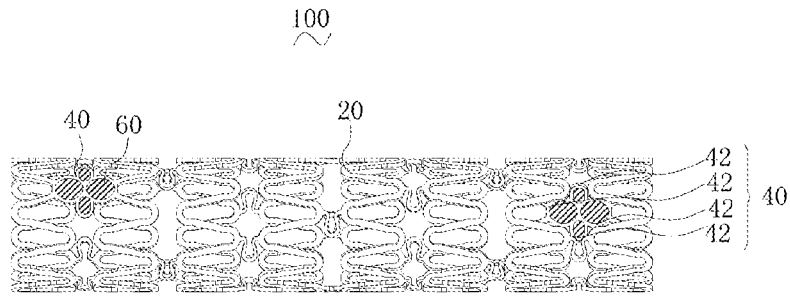
FIG. 1 is a schematic structural diagram of a stent according to an embodiment.

Referring to FIG. 1, a stent 100 according to an embodiment includes a stent substrate 20 and a radiopaque structure 40 disposed on the stent substrate 20.

In this embodiment, the stent substrate 20 has a hollowed-out lumen structure. It can be understood that, in other embodiments, the stent substrate 20 may also have other structures, such as a partially hollowed-out lumen structure, or a non-hollowed-out lumen structure.

The stent substrate 20 is a metal-based material. Any metal material that has better biocompatibility with the human body (or other desired characteristics) and can meet the mechanical properties of the stent can be used to form the stent substrate 20. For example, the stent substrate 20 may be a degradable metal-based material or a non-degradable metal-based material. In a further example, the stent substrate 20 is a magnesium-based alloy substrate, a zinc-based alloy substrate, an iron-based substrate, a pure iron substrate, a stainless steel substrate or the like.

In other embodiments, the stent substrate 20 may be a polymer-based material. Any polymer material that has better biocompatibility with the human body (or other desired characteristics) and can meet the mechanical properties of the stent can be used to form the stent substrate 20. There is at least one radiopaque structure 40. For example, in this embodiment, there are two radiopaque structures 40. The two radiopaque structures 40 are respectively disposed on two ends of the stent substrate 20.

It can be understood that the number of the radiopaque structures 40 is not limited to one or two, and the number of the radiopaque structures 40 can be set reasonably according to the shape, cross-sectional area of the radiopaque structures 40, length of the stent substrate 20, and the like. The arrangement of the radiopaque structures 40 is not limited to proximal and distal ends of the stent substrate 20, and the radiopaque structures 40 can be reasonably arranged according to the shape, cross-sectional area, and development definition requirements of the radiopaque structures 40. For example, the radiopaque structures 40 may be disposed in the middle of the stent substrate 20; or, one radiopaque structure 40 is disposed at the proximal end or the distal end of the stent substrate 20, and the other radiopaque structure 40 is disposed in the middle of the stent substrate 20, and the like.

Each radiopaque structure 40 includes at least one radiopaque unit 42, and a radiopaque material 60 is inlaid in the radiopaque unit 42. The radiopaque material 60 is inlaid in the radiopaque unit by thermal expansion and cold shrinkage of the blocky radiopaque material. That is, the blocky radiopaque material is first shrunk by cold and then thermally expanded, so that the blocky radiopaque material naturally expands to form the radiopaque body 60 that is in interference fit with the radiopaque unit 42 and thus inlaid in the radiopaque unit 42.

For example, in this embodiment, each radiopaque unit 62 has a through-hole structure.

It can be understood that the through-hole of the radiopaque unit 62 may be in a shape of a cylinder, a rectangular parallelepiped, a cube, a column with an elliptical cross section, a column with a triangular cross section, or the like. It can be understood that the shape of the radiopaque material 60 matches the radiopaque unit 42 in shape.

For example, a projection area of the radiopaque material 60 in the X-ray incident direction is less than or equal to 0.5 mm$^2$, thereby ensuring the developing effect, without affecting the mechanical properties of the stent 100 due to the too large area of the radiopaque material 60.

In this embodiment, each radiopaque structure 40 includes four radiopaque units 42, the four radiopaque units 42 being arranged in a petal shape. The four developing bodies 60 are in interference fit with the four radiopaque units 42 respectively by thermal expansion and cold shrinkage and thus inlaid into the four radiopaque units 42.

For example, the four radiopaque units 42 are symmetrically arranged at a common midpoint pairwise and have a petal shape, and the cross section of each radiopaque unit 42 is elliptic. The cross-sectional areas of two symmetric radiopaque units 42 are the same, both of which are S1; and the other two symmetric radiopaque units 42 have the same cross-sectional area, both of which are S2, S1 is larger than S2. The developing effect of such arrangement is better, and the mechanical properties of the stent substrate 20 itself are not affected substantially.

For example, a volume ratio of the volume of the radiopaque material 60 to the volume of the radiopaque unit 42 is 1.1 to 1.4, so that the binding force between the radiopaque material 60 and the radiopaque unit 42 is relatively strong, and it is ensured that the shape and position of the stent 100 can be recognized under a imaging device. When the wall thickness of the stent substrate 20 is less than 70 microns, a ratio of the volume of the radiopaque material 60 to the volume of the radiopaque unit 42 may be 1.2 to 1.4. For a stent having a wall thickness of less than 70 microns, because the wall thickness is relatively small, the bonding surface between the radiopaque unit 42 and the radiopaque material 60 in a radial direction of the stent substrate 20 is relatively small, and the radiopaque material 60 is liable to drop. When this ratio is set to 1.2 to 1.4, on the one hand, the radiopaque material 60 is appropriately in interference fit with the radiopaque unit 42 so that the bonding force between the radiopaque material 60 and the radiopaque unit 42 is relatively strong, and, on the other hand, it is ensured that the radiopaque material 60 will not crack or break the radiopaque unit 42.

The radiopaque material is selected from at least one of gold, platinum, osmium, rhenium, tungsten, iridium, rhodium, tantalum, barium sulfate, niobium trioxide, titanium oxide, zirconia, elemental iodine, and iodide. The radiopaque materials listed above have good developability. It can be understood that when the radiopaque material is a mixture of at least two kinds of the materials, a mass ratio of the at least two kinds of materials can be arbitrarily set. Regardless of one kind of the radiopaque material or at least two kinds of the radiopaque materials being selected, the radiopacity can be improved.

In a further embodiment, the radiopaque material 60 includes a radiopaque material and a binder. The radiopaque material is selected from at least one of gold, platinum, osmium, rhenium, tungsten, iridium, rhodium, tantalum, barium sulfate, niobium trioxide, titanium oxide, zirconia, elemental iodine, and iodide. The binder is a degradable polymer, which is selected from at least one of poly-L-lactic acid (PLLA), polyglycolide (PGLA), or poly(DL-lactic acid) (PDLLA).

The binder plays a binding role to bind the radiopaque materials together. During the preparation of the stent, the binder is subjected to thermal expansion after cold shrinkage, so that the radiopaque material 60 is in interference fit with the radiopaque unit 42 better. In addition, the binder is a degradable polymer and can be degraded into non-toxic and harmless substances in a living body, so that the biocompatibility of the stent 100 and the living body is better.

For example, the mass percentage of the binder is at least 20% or more.

The radiopaque material 60 of the stent 100 is embedded into the radiopaque unit 42, and the ratio of the volume of the radiopaque material 60 to the volume of the radiopaque unit 42 is 1.1 to 1.4. In this way, the interference fit between the radiopaque material 60 and the radiopaque unit 42 can be better achieved, so that the radiopaque material 60 and the radiopaque unit 42 have a stronger bonding force, and the problem of embolism caused by the drop of the radiopaque material is avoided.

In addition, the radiopaque material 60 of the stent 100 is inlaid in the radiopaque unit 42 by thermal expansion and cold shrinkage of the blocky radiopaque material. That is, the blocky radiopaque material is first shrunk by cold and then thermally expanded, so that the blocky radiopaque material is in interference fit with the radiopaque unit 42 of natural expansion and thus inlaid in the radiopaque unit 42. Such method can avoid mechanical damage caused by mechanical pressure riveting using a riveting needle, and can achieve an interference fit between the radiopaque material 60 and the radiopaque unit 42 and avoid the problem of embolism caused by the drop of the radiopaque material, thereby ensuring that the risk of thrombus or embolism introduced by the radiopaque material during and after implantation of the stent is extremely low.

Further, the blocky radiopaque material expands evenly during the natural temperature rise process without causing a deformation of the radiopaque material 60. The radiopaque material 60 and the radiopaque unit 42 are perfectly matched in shape. The radiopaque material 60 is seamlessly and intactly inlaid in the corresponding radiopaque unit 42 and is firmly combined with the radiopaque unit 42 so as not to fall off as a whole, thereby greatly improving the safety of the stent 100 implanted into the living body.

For example, the wall thickness of the stent substrate is less than or equal to 150 microns. For example, the wall thickness of the stent substrate is less than or equal to 70 microns. The ratio of the volume of the radiopaque material 60 to the volume of the radiopaque unit 42 is 1.2 to 1.4, so that the radiopaque material 60 and the radiopaque unit 42 achieve a tighter interference fit. Therefore, the problem that a radiopaque body is easily detached from a radiopaque structure when a radiopaque material is pressed in by using a conventional mechanical pressure riveting method to form the radiopaque body in the thin-wall stent can be solved.

Further, a preparation method for a stent is provided to prepare the stent 100.

Figure 2:
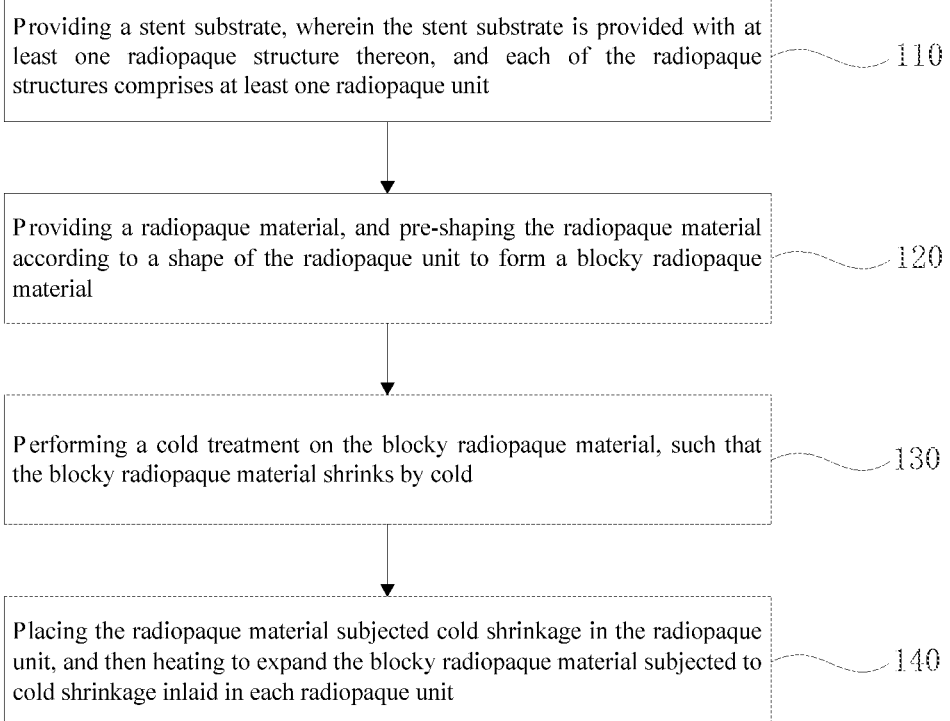
FIG. 2 is a flowchart of a preparation method for a stent according to an embodiment.

Referring to FIG. 2, a preparation method for a stent in an embodiment includes the following steps.

In S110, a stent substrate is provided, where the stent substrate is provided with at least one radiopaque structure thereon, and each of the radiopaque structures includes at least one radiopaque unit.

The stent substrate can be formed by cutting a tubular material with laser. The stent substrate is provided with at least one radiopaque structure thereon, and each of the radiopaque structures includes at least one radiopaque unit. In this embodiment, the stent substrate and the radiopaque structure are integrally formed. It can be understood that, in other embodiments, the radiopaque structure may be disposed on the stent substrate by welding or winding.

In S120, a radiopaque material is provided, and the radiopaque material is pre-shaped according to a shape of the radiopaque unit to form a blocky radiopaque material.

The radiopaque material is the radiopaque material described above, and will not be repeated here. It can be understood that, in the embodiment in which the radiopaque body further includes a binder, the radiopaque material is mixed with the binder and then preshaped.

For example, the radiopaque material is pre-shaped into the blocky material that matches the radiopaque unit in shape through a mold. The shape and size of the radiopaque material can be better controlled by pre-shaping with a mold so as to perfectly match the radiopaque unit. The size of the blocky radiopaque material in the normal direction of the contact surface is larger than the size of the radiopaque unit in the normal direction of the contact surface. In this case, the blocky radiopaque material cannot be inlaid in the radiopaque unit at room temperature.

In S130, a cold treatment is performed on the blocky radiopaque material, such that the blocky radiopaque material shrinks by cold.

For example, the blocky radiopaque material is placed in a low-temperature environment and subjected to cold treatment, so that the blocky radiopaque material shrinks in size by cold, that is, cold shrinkage.

For example, the temperature of the low-temperature environment, that is, the temperature of the cold treatment is −20° C. to −80° C. Further, the time for the cold treatment can be greater than or equal to 30 min, so as to ensure that the blocky radiopaque material is sufficiently thermally balanced with the environment, so that its size shrinks to a certain degree, thereby facilitating the material to thermally expand and be in interference fit with the radiopaque structure in the subsequent heat treatment step.

It can be understood that the temperature of the cold treatment is not limited to −20° C. to −80° C., and any low temperature capable of causing the blocky radiopaque material to shrink to be accommodated into the radiopaque unit due to its own gravity is available. The cold treatment time is not limited to be greater than or equal to 30 minutes, and any treatment time that can make the blocky radiopaque material reach a temperature balance with the low temperature environment is available. It can also be understood that, on the one hand, the stent undergoes a variety of processing techniques in actual production, such as polishing, and therefore, the actual shape of the radiopaque unit of the stent may be slightly different from a standard shape; or the pre-shaping of the radiopaque material is not perfect enough, and thus the shape of the radiopaque material is slightly different from the shape of the radiopaque unit. However, these differences cannot be recognized under a microscope. On the other hand, the struts and the blocky radiopaque material of the actual stent have a certain thickness, and thus there is a certain error in the measurement. In this case, the blocky radiopaque material cannot be accommodated into the radiopaque unit due to its own gravity after the cold treatment, but can be accommodated into the radiopaque structure by applying a slight external force to knock slightly. Therefore, any low temperature capable of enabling the blocky radiopaque material to be accommodated into the radiopaque unit due to a slight external force is available.

In S140, the radiopaque material subjected cold shrinkage is placed in the radiopaque unit, and then heated to expand the blocky radiopaque material subjected to cold shrinkage to form a radiopaque body inlaid in the radiopaque unit.

Under a microscope, the blocky radiopaque material subjected to cold shrinkage is quickly placed in the radiopaque unit, and a heat treatment is then performed by the thermal expansion and cold shrinkage properties of the radiopaque material, such that the blocky radiopaque material subjected to cold shrinkage expands thermally. After being heated, the blocky radiopaque material expands in volume and is firmly inlaid in the radiopaque unit.

For example, the step of heating refers to naturally warming up to room temperature so as to ensure the uniformity of thermal expansion of the radiopaque material. When the radiopaque material returns to room temperature, the radiopaque material gradually and uniformly expands in volume. Finally, at room temperature, the blocky radiopaque material seamlessly and intactly forms a radiopaque body inlaid in the radiopaque structure.

In the preparation method for the stent, the radiopaque material is filled into the radiopaque unit of the stent by using the properties of thermal expansion and cold shrinkage of the radiopaque material. Such non-mechanical pressure riveting method can make the radiopaque body well attached to the radiopaque unit without causing damage to the surface of the stent, thereby greatly increasing the product qualification rate while reducing the risk of the drop of the radiopaque material during or after implantation.

In addition, the efficiency of the preparation method for the stent is higher than that of the traditional mechanical pressure riveting, and the preparation efficiency is greatly improved.

The above-mentioned stent and the preparation method therefor will be described below through various examples.

The following test and calculation methods are used in the following examples:

1. A microscope (Keyence, VHX-700F or SENSOFAR, Q6) is used to test the size of the radiopaque unit of the radiopaque structure.

2. There are two methods to calculate the volume of the blocky radiopaque material:

(1) when the radiopaque material is a single substance, the blocky radiopaque material can be directly weighed and its mass m is recorded; the density $\rho$ of the blocky radiopaque material can be obtained by references, and the volume of the blocky radiopaque material can be calculated using a formula $v=m/\rho$; and (2) when the radiopaque material is a mixed substance, the size of the blocky radiopaque material is tested with a microscope, and an appropriate formula is selected to calculate the volume of the blocky radiopaque material according to the shape of the radiopaque material.

The appropriate formula means that for a blocky radiopaque material with a regular shape, a corresponding volume calculation formula is adopted, such as a volume calculation formula of a cylinder; and for an irregular blocky radiopaque material, integrals are used to calculate its volume.

3. The surface condition of the radiopaque body of the stent is observed with a microscope (Keyence, VHX-700F).

Example 1

An iron-based alloy vascular stent with a wall thickness of 0.03 mm includes a radiopaque structure. The radiopaque structure includes only one radiopaque unit, and the radiopaque unit has a cylindrical through-hole structure. The through hole has a diameter 0.618 mm, and a volume of 0.009 mm$^3$. A radiopaque material is pre-shaped in a mold to form a blocky radiopaque material having a cylindrical shape. The cylinder has a diameter of 0.620 mm and a volume of 0.0126 mm$^3$. The radiopaque material is formed only of gold. The blocky radiopaque material is placed in a refrigerator at −80° C. for 0.5 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 0.05%, thereby greatly increasing the product qualification rate.

Example 2

An iron-based alloy vascular stent with a wall thickness of 0.053 mm includes a radiopaque structure. The radiopaque structure includes only one radiopaque unit, and the radiopaque unit has a cylindrical through-hole structure. The through hole has a diameter 0.485 mm, and a volume of 0.009805 mm$^3$. A radiopaque material is pre-shaped in a mold to form a blocky radiopaque material having a cylindrical shape. The cylinder has a diameter of 0.487 mm and a volume of 0.012747 mm$^3$. The radiopaque material is formed only of gold. The blocky radiopaque material is placed in a refrigerator at −80° C. for 1 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 0.04%, thereby greatly increasing the product qualification rate.

Example 3

An iron-based alloy vascular stent with a wall thickness of 0.07 mm includes two radiopaque structures which are located on the proximal and distal ends of a stent substrate. Each of the two radiopaque structures includes only one radiopaque unit, and each radiopaque unit has a cylindrical through-hole structure. The through hole has a diameter 0.416 mm, and a volume of 0.00952 mm$^3$. A radiopaque material is pre-shaped in a mold to form a blocky radiopaque material having a cylindrical shape. The cylinder has a diameter of 0.418 mm and a volume of 0.011424 mm$^3$. A radiopaque material is formed only of gold. The blocky radiopaque material is placed in a refrigerator at −80° C. for 1 h, and then quickly placed in each radiopaque unit under a microscope, and then naturally warmed up. When the radiopaque material reaches a balance with the room temperature, the blocky radiopaque material firmly fixed in each radiopaque unit. As observed through the microscope, the surfaces of the radiopaque material and the radiopaque structures are smooth and free of abrasion. The drop rate of the radiopaque material during ultrasonic cleaning is reduced from 5% of the original mechanical pressure riveting method to 0.03%, thereby greatly increasing the product qualification rate.

Example 4

An iron-based alloy vascular stent with a wall thickness of 0.1 mm includes a radiopaque structure. The radiopaque structure includes only one radiopaque unit, and the radiopaque unit has a cylindrical through-hole structure. The through hole has a diameter of 0.359 mm, and a volume of 0.0101 mm$^3$. The radiopaque material is pre-shaped in a mold to form a blocky radiopaque material having a cylindrical shape. The cylinder has a diameter of 0.36 mm and a volume of 0.01111 mm$^3$. A radiopaque material is formed only of gold. The blocky radiopaque material is placed in a refrigerator at −80° C. for 1 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 0.03%, thereby greatly increasing the product qualification rate.

Example 5

A magnesium-based alloy vascular stent with a wall thickness of 0.12 mm includes a radiopaque structure. The radiopaque structure includes only one radiopaque unit, and the radiopaque unit has a cylindrical through-hole structure. The through hole has a diameter 0.331 mm, and a volume of 0.01032 mm$^3$. A radiopaque material is pre-shaped in a mold to form a blocky radiopaque material having a cylindrical shape. The cylinder has a diameter of 0.332 mm and a volume of 0.011352 mm$^3$. The radiopaque material is formed only of gold. The blocky radiopaque material is placed in a refrigerator at −80° C. for 1 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 0.02%, thereby greatly increasing the product qualification rate.

Example 6

A polylactic acid vascular stent with a wall thickness of 0.15 mm includes a radiopaque structure. The radiopaque structure includes only one radiopaque unit, and the radiopaque unit has a cylindrical through-hole structure. The through hole has a diameter 0.301 mm, and a volume of 0.010635 mm$^3$. A radiopaque material is pre-shaped in a mold to form a blocky radiopaque material having a cylindrical shape. The cylinder has a diameter of 0.302 mm and a volume is 0.011699 mm$^3$. The radiopaque material is formed only of gold and platinum according to a mass ratio of 1:1. The blocky radiopaque material is placed in a refrigerator at −80° C. for 1 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 0.01%, thereby greatly increasing the product qualification rate.

Example 7

An iron-based alloy vascular stent with a wall thickness of 0.053 mm includes a radiopaque structure. The radiopaque structure is formed of four adjacent radiopaque units. The four radiopaque units are of a through-hole structure respectively, in which the areas are equal in pairs and the cross-sections are elliptic, and the four radiopaque units are symmetrically arranged pairwise at a common midpoint. The two larger and equal radiopaque units have a major axis length of 0.36 mm, a minor axis length of 0.3 mm, and a volume of 0.004493 mm$^3$ respectively; and the two smaller and equal radiopaque units have a major axis length of 0.25 mm, a minor axis length of 0.2 mm, and a volume of 0.00208 mm$^3$ respectively. A radiopaque material is pre-shaped in a mold to form a cylinder having an elliptic cross-section. The larger elliptical cylindrical radiopaque material has a major axis of 0.363 mm, a minor axis of 0.303 mm, and a volume of 0.005392 mm$^3$; and the smaller elliptical cylindrical radiopaque material has a long axis of 0.252 mm, a short axis of 0.202 mm, and a volume of 0.002496 mm$^3$. The radiopaque material is formed only of gold. The four blocky radiopaque materials are placed in a refrigerator at −80° C. for 1 h, and then quickly placed in the radiopaque unit under a microscope, and then naturally warmed up. When the radiopaque material reaches a balance with the room temperature, the four blocky radiopaque materials firmly fixed in the respective radiopaque unit respectively. As observed through the microscope, the surfaces of the four blocky radiopaque materials and the radiopaque structure are smooth and free of abrasion. The drop rate of the radiopaque material during ultrasonic cleaning is reduced from 5% of the original mechanical pressure riveting method to 0.02%, thereby greatly increasing the product qualification rate.

Example 8

A zinc-based alloy vascular stent with a wall thickness of 0.1 mm includes a radiopaque structure. The radiopaque structure includes only one radiopaque unit, and the radiopaque unit has a cylindrical through-hole structure. The through hole has a diameter 0.359 mm, and a volume of 0.0101 mm$^3$. A radiopaque material is pre-shaped in a mold to form a blocky radiopaque material having a cylindrical shape. The cylinder has a diameter of 0.362 mm and a volume of 0.011615 mm$^3$. The radiopaque material is formed of a mixture of gold powder and polylactic acid (where the mass percentage of polylactic acid is 30%). The radiopaque material is placed in a refrigerator at −20° C. for 2 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 0.05%, thereby greatly increasing the product qualification rate.

Example 9

An iron-based alloy vascular stent with a wall thickness of 0.053 mm includes a radiopaque structure. The radiopaque structure includes only one radiopaque unit, and the radiopaque unit has a cylindrical through-hole structure. The through hole has a diameter 0.485 mm, and a volume of 0.009805 mm$^3$. A radiopaque material is pre-shaped in a mold to form a blocky radiopaque material having a cylindrical shape. The cylinder has a diameter of 0.487 mm and a volume is 0.012256 mm$^3$. The radiopaque material is formed only of gold. The blocky radiopaque material is placed in a refrigerator at −60° C. for 1.5 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 2%, thereby greatly increasing the product qualification rate.

Example 10

A pure iron vascular stent with a wall thickness of 0.12 mm includes a radiopaque structure. The radiopaque structure includes only one radiopaque unit, and the radiopaque unit has a cylindrical through-hole structure. The through hole has a diameter of 0.8 mm, and a volume of 0.06029 mm$^3$. A radiopaque material is pre-shaped in a mold to form a blocky radiopaque material having a cylindrical shape. The cylinder has a diameter of 0.801 mm and a volume of 0.06632 mm$^3$. The radiopaque material is formed only of zirconia. The blocky radiopaque material is placed in a refrigerator at −80° C. for 1 h, and then quickly placed in the radiopaque unit under a microscope, and then naturally warmed up. When the radiopaque material reaches a balance with the room temperature, the blocky radiopaque material firmly fixed in the radiopaque unit. As observed through the microscope, the surfaces of the radiopaque material and the radiopaque structure are smooth and free of abrasion. The drop rate of the radiopaque material during ultrasonic cleaning is reduced from 5% of the original mechanical pressure riveting method to 0.02%, thereby greatly increasing the product qualification rate. The technical features of the above-described embodiments may be combined, as desired. For the sake of brevity of description, all possible combinations of the technical features in the above embodiments are not described. However, they should be considered as the scope of the description.

The above-described embodiments are merely illustrative of several embodiments of the present disclosure, and the description thereof is more specific and detailed, but is not to be construed as limiting the scope of the present disclosure. It should be noted that a number of variations and modifications may be made by those of ordinary skill in the art without departing from the concept of the present disclosure, all of which should fall within the protection scope of the present invention.

The invention claimed is:
1. A stent, comprising:
   a stent substrate, the stent substrate provided with at least one radiopaque structure thereon, and each of the radiopaque structures comprises at least one radiopaque unit, and a radiopaque material is inlaid in each of the radiopaque units; and a ratio of the volume of the radiopaque material to the volume of the radiopaque unit is 1.1 to 1.4,
   wherein each of the radiopaque structures consists of four radiopaque units, the four radiopaque units being arranged in a petal shape.
2. The stent according to claim 1, wherein a ratio of the volume of the radiopaque material to the volume of the radiopaque unit is 1.2 to 1.4.

3. The stent according to claim 1, further comprising two radiopaque structures which are respectively disposed at two ends of the stent substrate.

4. The stent according to claim 1, wherein the radiopaque material is selected from at least one of a group consisting of gold, platinum, osmium, rhenium, tungsten, iridium, rhodium, tantalum, barium sulfate, niobium trioxide, titanium oxide, zirconia, elemental iodine, and iodide.

5. The stent according to claim 1, wherein each radiopaque material further comprises a binder, and the binder is a degradable polymer.

6. The stent according to claim 1, wherein the wall thickness of the stent substrate is less than or equal to 150 microns.

7. The stent according to claim 1, wherein the wall thickness of the stent substrate is less than or equal to 70 microns.

8. The stent according to claim 1, wherein a projection area of radiopaque material in an X-ray incident direction is less than or equal to 0.5 mm$^2$.

9. The stent according to claim 1, wherein the radiopaque material has a cylindrical shape.

* * * * *